United States Patent [19]

Opalka, Jr. et al.

[11] 4,223,149
[45] Sep. 16, 1980

[54] PROCESS FOR PRODUCING 3-CYANO-5-(PYRIDINYL)-2(1H)-PYRIDINONES

[75] Inventors: Chester J. Opalka, Jr.; George Y. Lesher, both of Schodack, N.Y.

[73] Assignee: Sterling Drug Inc., New York, N.Y.

[21] Appl. No.: 60,758

[22] Filed: Jul. 26, 1979

[51] Int. Cl.$^2$ ............................................. C07D 401/04
[52] U.S. Cl. ..................................................... 546/257
[58] Field of Search ........................................ 546/257

[56] References Cited

U.S. PATENT DOCUMENTS

| 4,004,012 | 1/1977 | Lesher et al. | 546/257 |
| 4,107,315 | 8/1978 | Lesher et al. | 546/257 |

OTHER PUBLICATIONS

Nantkanamirski et al., "Polish-J. Pharmacol Pharmacy" vol. 30, No. 5, pp. 707–712 (1978).

Primary Examiner—Henry R. Jiles
Assistant Examiner—Robert T. Bond
Attorney, Agent, or Firm—R. K. Bair; B. W. Wyatt

[57] ABSTRACT

A process for preparing 1,2-dihydro-2-oxo-5-(pyridinyl) nicotinonitriles by reacting α-(pyridinyl)-β-[di-(loweralkyl)amino]acrolein with malononitrile in a loweralkanol. The products are useful as cardiotonic agents and, also, as intermediates for preparing corresponding 3-amino-5-(pyridinyl-2(1H)-pyridinones, in turn, useful as cardiotonic agents.

5 Claims, No Drawings

PROCESS FOR PRODUCING 3-CYANO-5-(PYRIDINYL)-2(1H)-PYRIDINONES

BACKGROUND OF THE INVENTION (a) Field of the Invention

This invention relates to an improved method for preparing 5-(pyridinyl)nicotinonitriles.

The Lesher and Opalka U.S. Pat. No. 4,004,012, issued Jan. 18, 1977, shows two methods of preparing 1,2-dihydro-2-oxo-5-(pyridinyl)nicotinonitriles and conversion by hydrolysis to the corresponding nicotinamides and, in turn, the conversion of the nicotinamides to the corresponding 3-amino compounds. These methods are presented structurally in columns 3 and 4 of U.S. Pat. No. 4,004,012. Note in particular the two methods for preparing 1,2-dihydro-2-oxo-5-(pyridinyl)-nicotinonitriles (III in patent), i.e., (1) by reacting α-(pyridinyl)-β-($R_1R_2N$)acrolein with α-cyanoacetamide in the presence of a basic condensing agent, preferably an alkali lower-alkoxide, e.g., sodium methoxide or sodium ethoxide, in a lower-alkanol, e.g., methanol or ethanol; and, (2) by heating α-(pyridinyl)malonaldehyde with α-cyanoacetamide in the presence of a catalytic condensing agent, preferably morpholine or piperidine and/or its acetate. As shown in Example A-1 in the paragraph common to columns 9 and 10 of U.S. Pat. No. 4,004,012, the product in method (1) is collected as its sodium salt, recrystallized and then coverted by treatment with hydrochloric acid to 1,2-dihydro-2-oxo-5-(pyridinyl)nicotinonitrile.

A recently published abstract ["Current Abstracts of Chemistry", Vol. 74, Issue 814, Item 285573, 1979] of a Polish publication [Nantkanomirski and Kaczmarek, Polish J. Pharmacol. Pharmacy 30(5), 707–12 (1978)] shows, inter alia, the reaction of 3-dimethylamino-2-(4-pyridinyl)acrolein [same as α-(4-pyridinyl)-β-(dimethylamino)acrolein] with malononitrile in the presence of sodium methoxide in methanol to poduce 2-methoxy-5-(4-pyridinyl)nicotinonitrile.

SUMMARY OF THE INVENTION

The invention relates to the process of preparing 1,2-dihydro-2-oxo-5(pyridinyl)nicotinonitriles by reacting α-pyridinyl-β-(dialkylamino)acrolein with malononitrile in a lower-alkanol.

DETAILED DESCRIPTION INCLUSIVE OF PREFERRED EMBODIMENTS

The invention resides in the process which comprises reacting α-pyridinyl-β-[di-(lower-alkyl)amino]acrolein with malononitrile in a lower-alkanol to produce 1,2-dihydro-2-oxo-5-(pyridinyl)nicotinonitrile where pyridinyl is 4- or 3- or 2-pyridinyl or 4- or 3- or 2-pyridinyl having one or two lower-alkyl substituents. In preferred embodiments pyridinyl is 4- or 3-pyridinyl and lower-alkyl in the intermediate acrolein derivative is methyl or ethyl. The lower-alkanol preferably used is ethanol or isopropyl alcohol, the latter preferably containing about 5 to 10% water. The ethanol can be 100% or 95% ethanol. The products produced by the process are useful as cardiotonic agents (U.S. Pat. No. 4,004,012) and as intermediates in the preparation of 3-amino-5-(pyridinyl)-2(1H)-pyridinones (U.S. Pat. Nos. 4,004,012 and 4,072,746). The process is a decided improvement over the prior art method which uses cyanoacetamide since the product in the instant process is obtained directly from the reaction mixture in sufficiently pure form for use in preparing the corresponding 3-carbamyl and then 3-amino compounds; in contrast, the prior art method using cyanoacetamide in the presence of sodium methoxide or ethoxide in methanol or ethanol produces the sodium salt of 1,2-dihydro-2-oxo-5-(pyridinyl)nicotinonitrile which not only is difficult to filter and wash but also must undergo an additional acid-treatment step to obtain the product. No catalyst is needed in the process of the instant invention.

The term "lower-alkyl" as used herein, e.g., as a substituent for "pyridinyl" or in "di-(lower-alkyl)amino" in the intermediate acrolein, means alkyl radicals having from one to four carbon atoms which can be arranged as straight or branched claims, illustrated by methyl, ethyl, n-propyl, isopropyl, n-butyl, 2-butyl or isobutyl.

The term "pyridinyl" as used here, e.g., as the α-substituent in the intermediate acrolein and as the 5-substituent of the final product, means 4- or 3- or 2-pyridinyl or 4- or 3- or 2-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 4methyl-2-pyridinyl, 6-methyl-2-pyridinyl, 2,3-dimethyl-4-pyridinyl, 2,6-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, and the like.

The term "lower-alkanol" as used herein as the solvent in which the process of the invention is carried out has from one to four carbon atoms which can be arranged as straight or branched claims, illustrated by methanol, ethanol, n-propanol, 2-propanol, n-butanol, 2-butanol and 2-methyl-n-propanol.

The molecular structures of the products produced by the process of the invention were assigned on the basis of evidence provided by infrared, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows:

The process of the invention is carried out by reacting an α-(pyridinyl)-β-[di-(lower-alkyl)amino]acrolein with malononitrile in a lower-alkanol. The reaction is carried out preferably by heating the reactants as about 60°–118° C., preferably about 75°–95° C., preferably using ethanol or 2-propanol, the latter preferably containing about 5 to 10% (by volume) of water to increase the solubility of malononitrile. The reaction is conveniently carried out using either 100% or 95% ethanol.

The following examples will further illustrate the invention without, however, limiting it thereto.

EXAMPLE 1

A mixture containing 17.6 g of α-(4-pyridinyl)-β-(diethylamino)acrolein, 9.9 g of malonitrile and 700 ml of absolute ethanol was refluxed for one hour and then allowed to cool to room temperature. The separated product was collected, washed successively with ethanol and ether, and dried to yield 15 g of 1,2-dihydro-2-oxo-5-(4-pyridinyl)-nicotinonitrile, m.p. >300° C. The above procedure was also carried out using 95% ethanol.

Following the procedures described in Example 1 but using in place of α-(4-pyridinyl)-β-(diethylamino)acrolein a molar equivalent quantity of the appropriate α-(pyridinyl)-βdimethylaminoacrolein, the following 1,2-dihydro-2-oxo-5-(pyridinyl)nicotinonitriles are obtained: 1,2-dihydro-2-oxo-5-(3-pyridinyl)nicotinonitrile using α-(3-pyridinyl)-β-dimethylaminoacrolein; 1,2-dihydro-2-oxo-5-(2methyl-3-pyridinyl)nicotinonitrile using α-(2methyl-3-pyridinyl)-β-dimethylaminoacrolein; 1,2-dihydro-2-oxo-5-(3ethyl-4-pyridinyl)-nicotinonitrile using α-(3-ethyl-4-pyridinyl)-β-dimethylaminoacrolein; and, 1,2-dihydro-2-oxo-5-(4,6-dimethyl-2-pyridinyl) nicotinonitrile using α-(4,6-dimethyl-2-pyridinyl)-β-dimethylaminoacrolein.

EXAMPLE 2

A mixture containing 8.8 g of α-(4-pyridinyl)-β-(dimethylamino)acrolein, 4g of malononitrile in 100 ml of ethanol was refluxed for one hour, allowed to cool and the precipitate collected. The precipitate was washed successively with ethanol and ether, dried, recrystallized from dimethylformamide, washed successively with ethanol and ether, and dried to yield 6 g of 1,2-dihydro-2-oxo-5-(4-pyridinyl)-nicotinonitrile, m.p.>300° C. The nuclear magnetic resonance spectral data and TLC (3:1 ethyl acetate:methanol on silica) of the compound was consistent with that of the same compound prepared by a different manner.

EXAMPLE 3

To 2500 ml of isopropyl alcohol heated to reflux was added with stirring 300 g of 3-dimethylamino-2-(4-pyridinyl)-2-propen-1-one [same as α-(4-pyridinyl)-β-(dimethyl-amino)acrolein]. To the resulting mixture was added 500 ml of a solution containing 138 g of malonontrile, 1500 ml of isopropyl alcohol and 100 ml of water. The temperature was brought back to reflux in about 10 minutes and then the remainder of the malononitrile solution was added from a dropping funnel over a period of about 25 minutes. The reaction mixture was stirred at reflux for additional 35 minutes and the resulting orange suspension was cooled to 3° C. The precipitated solid was collected by filtration and the filter cake was washed with four 100 ml portions of cold isopropyl alcohol. The solid was then dried at 40° C. in vacuo overnight (about 15 hours) and then for two hours at 60° C. to yield 245 g of 5-cyano[3,4'-bipyridin]-6(1H)-one [same as 1,2-dihydro-2-oxo-5-(4-pyridinyl)-nicotinonitrile], m.p.>300° C. The nuclear magnetic resonance spectrum of this product was consistent with that of the same product prepared by another method. The filtrate was concentrated in vacuo to about 500 ml volume and cooled in an ice bath. A total of 40 g of a second crop material was obtained, m.p.>300° C.

We claim:

1. The process which comprises reacting α-(pyridinyl)-β-[di-(lower-alkyl)amino]acrolein with malononitrile in a lower alkanol to produce 1,2-dihydro-2-oxo-5-(pyridinyl)nicotinonitrile.

2. The process according to claim 1 where the reaction is carried out in refluxing ethanol.

3. The process according to claim 1 where the reaction is carried out in refluxing isopropyl alcohol containing about 5 to 10% water.

4. The process according to claim 2 where α-(4-pyridinyl)-β-(dimethylamino)acrolein is used to produce 1,2-dihydro-2-oxo-5-(4-pyridinyl)nicotinonitrile.

5. The process according to claim 3 where α-(4-pyridinyl)-β-(dimethylamino)acrolein is used to produce 1,2-dihydro-2-oxo-5-(4-pyridinyl)nicotinonitrile.

* * * * *